US007217254B2

United States Patent
Kirwan et al.

(12) United States Patent
(10) Patent No.: US 7,217,254 B2
(45) Date of Patent: May 15, 2007

(54) MULTI-PRESSURE BIOCOMPATIBLE AGENT DELIVERY DEVICE AND METHOD

(75) Inventors: John M. Kirwan, North Andover, MA (US); Joseph Jeffrey Kablik, Tyngsboro, MA (US)

(73) Assignee: Genzyme Corporation, Cambridge, MA (US)

( * ) Notice: Subject to any disclaimer, the term of this patent is extended or adjusted under 35 U.S.C. 154(b) by 606 days.

(21) Appl. No.: 10/251,618

(22) Filed: Sep. 20, 2002

(65) Prior Publication Data
US 2004/0059283 A1 Mar. 25, 2004

(51) Int. Cl.
*A61M 37/00* (2006.01)
*A61M 5/00* (2006.01)

(52) U.S. Cl. .............................. 604/82; 604/191; 604/24

(58) Field of Classification Search ................... 604/82, 604/191, 141, 143, 147, 149, 23, 24, 26
See application file for complete search history.

(56) References Cited

U.S. PATENT DOCUMENTS

| | | | |
|---|---|---|---|
| 3,415,419 A | 12/1968 | Jewett et al. | |
| 3,749,090 A | 7/1973 | Stewart | |
| 3,880,158 A | 4/1975 | Gurney | |
| 3,987,000 A | 10/1976 | Gleichenhagen et al. | |
| 4,037,599 A | 7/1977 | Raulerson | |
| 4,040,420 A | 8/1977 | Speer | |
| 4,179,068 A | 12/1979 | Dombrowski | |
| 4,180,239 A | 12/1979 | Valukis | |
| 4,329,988 A | 5/1982 | Sarnoff et al. | |
| 4,673,395 A | 6/1987 | Phillips | |
| 4,735,616 A | 4/1988 | Eibl et al. | |
| 4,740,203 A | 4/1988 | Hoskins et al. | |
| 4,978,336 A | 12/1990 | Capozzi et al. | |
| 4,979,942 A | 12/1990 | Wolf et al. | |
| 5,022,563 A | 6/1991 | Marchitto et al. | |
| 5,104,375 A | 4/1992 | Wolf et al. | |
| 5,116,315 A | 5/1992 | Capozzi et al. | |

(Continued)

FOREIGN PATENT DOCUMENTS

EP 0 041 022 A1 12/1981

(Continued)

OTHER PUBLICATIONS

Ogawa et al., "Newly Devised Instrument for Spraying Aerosolized Fibrin Glue in Thoracoscopic Operations", *Ann. Thorac. Surg.*, 1993, vol. 55, pp. 1595-1596.

*Primary Examiner*—Catherine S. Williams
(74) *Attorney, Agent, or Firm*—Richard D. Allison; Thomas J. DesRosier (57) ABSTRACT

A device for application of material to a surface, for example, biocompatible material to a tissue surface in a medical or clinical setting, is adapted to receive one or more biocompatible materials and one or more sources of pressurized medical gas, and to deliver these biocompatible materials via the medical gas(es) to a tissue surface or other surface. A regulation system controls flow of medical gas at a variety of pressures, and flow of biocompatible agent or agents, allowing agents to be sprayed or otherwise deployed onto a tissue surface. Switching apparatus operably connected to the regulation system directs a set of preset treatment positions allowing sequential application of biocompatible materials under various conditions in conjunction with an overall treatment protocol. The device can be used to apply a photoinitiating primer and polymeric sealant to a tissue surface, followed by light activation to form a polymer coating on the surface. The device can easily be operated in a variety of orientations by a user, with switching apparatus arranged for logical, stepwise progression through the protocol in any orientation.

17 Claims, 8 Drawing Sheets

U.S. PATENT DOCUMENTS

| | | | |
|---|---|---|---|
| 5,126,141 A | 6/1992 | Henry | |
| 5,147,203 A | 9/1992 | Seidenberg | |
| 5,149,330 A | 9/1992 | Brightbill | |
| 5,222,939 A | 6/1993 | Tiefenbrun et al. | |
| 5,226,877 A | 7/1993 | Epstein | |
| 5,312,333 A | 5/1994 | Churinetz et al. | |
| 5,368,563 A | 11/1994 | Lonneman et al. | |
| 5,372,585 A | 12/1994 | Tiefenbrun et al. | |
| 5,410,016 A | 4/1995 | Hubbell et al. | |
| 5,470,311 A | 11/1995 | Setterstrom et al. | |
| 5,582,596 A | 12/1996 | Fukunaga et al. | |
| 5,605,541 A | 2/1997 | Holm | |
| 5,612,050 A | 3/1997 | Rowe et al. | |
| 5,665,067 A * | 9/1997 | Linder et al. | 604/82 |
| 5,698,189 A | 12/1997 | Rowe et al. | |
| 5,749,968 A | 5/1998 | Melanson et al. | |
| 5,759,169 A * | 6/1998 | Marx | 604/82 |
| 5,759,171 A | 6/1998 | Coelho et al. | |
| 5,800,373 A | 9/1998 | Melanson et al. | |
| 5,800,431 A | 9/1998 | Brown | |
| 5,800,538 A | 9/1998 | Slepian et al. | |
| 5,874,500 A | 2/1999 | Rhee et al. | |
| 5,895,412 A | 4/1999 | Tucker | |
| 6,004,547 A | 12/1999 | Rowe et al. | |
| 6,051,248 A | 4/2000 | Sawhney et al. | |
| 6,121,341 A | 9/2000 | Sawhney et al. | |
| 6,149,622 A | 11/2000 | Marie | |
| 6,150,581 A | 11/2000 | Jiang et al. | |
| 6,217,894 B1 | 4/2001 | Sawhney et al. | |
| D453,376 S | 2/2002 | McMahon et al. | |
| 6,352,710 B2 | 3/2002 | Sawhney et al. | |
| 6,387,977 B1 | 5/2002 | Sawhney et al. | |
| 6,468,520 B1 | 10/2002 | Rowe et al. | |
| 6,482,179 B1 | 11/2002 | Chu et al. | |
| D483,475 S | 12/2003 | Kirwan et al. | |
| 6,863,660 B2 * | 3/2005 | Marx | 604/147 |
| 2002/0198564 A1 * | 12/2002 | Pichon et al. | 606/214 |

FOREIGN PATENT DOCUMENTS

| | | |
|---|---|---|
| EP | 0 105 493 A2 | 4/1984 |
| EP | 0 249 186 A1 | 12/1987 |
| EP | 0 315 222 A2 | 5/1989 |
| WO | WO 90/01959 A1 | 3/1990 |
| WO | WO 90/01969 A1 | 3/1990 |
| WO | WO 92/21354 A1 | 10/1992 |
| WO | WO 93/16687 A1 | 9/1993 |
| WO | WO 93/17669 A1 | 9/1993 |
| WO | WO 94/21324 A1 | 9/1994 |
| WO | WO 96/29370 A2 | 9/1996 |
| WO | WO 97/36622 A1 | 10/1997 |
| WO | WO 98/20931 A1 | 5/1998 |
| WO | WO 99/34833 A1 | 7/1999 |
| WO | WO 00/06216 A1 | 2/2000 |
| WO | WO 00/15117 A1 | 3/2000 |
| WO | WO 02/051383 A2 | 7/2002 |

* cited by examiner

MULTI-PRESSURE BIOCOMPATIBLE AGENT DELIVERY DEVICE AND METHOD

FIELD OF THE INVENTION

This invention relates generally to apparatus for delivering one or more biocompatible agents to a surface, and more particularly to a device for delivery of biocompatible agents to tissue surfaces of patients via gas pressurized at two different levels.

BACKGROUND OF THE INVENTION

Medical devices are available for application of biocompatible agents to tissue surfaces. Devices range in type from those designed simply to extrude material from a reservoir directly onto a surface, to those able to spray material onto a surface and then to activate the material to change it in some way, for example by exposing it to polymerizing light. Devices exist that are designed to apply two or more agents to a tissue surface that react with each other spontaneously, or upon the application of light, to change harden.

Examples of devices for delivery of one or more agents to a tissue surface can be found in U.S. Pat. No. 5,582,596 (Fukunaga, et al.), U.S. Pat. No. 5,665,067 (Linder, et al.), U.S. Pat. No. 5,749,968 (Melenson, et al.), and in International Patent Application Serial No. PCT/US99/21521 (International Patent Publication WO 00/15117; Pichon, et al.). The latter (WO 00/15117) describes a gas-powered spraying device that can be used for single or multi-part reactive medical polymer compositions. In use, one or more fluids are sprayed independently at a tissue surface by introducing the fluids into a medical gas. The fluids can be stored in reservoirs which are attachable to the device at inlet ports fluidly connectable to an outlet of the device at which the fluids can be independently introduced into flowing gas and thereby delivered to the tissue surface. Gas flow is provided at two flow levels, including a high level flow for active spraying of material onto the tissue surface, and a low level flow to remove drips from the outlet and prevent clogging, to improve device reliability. In one arrangement, the two fluids are separately applied to a single tissue surface area at which they react to harden, spontaneously or photochemically.

In the above and other systems, it is often important to apply two or more fluids independently, and in some cases sequentially, to a tissue surface. In many cases it is desirable to apply fluids evenly or unevenly, depending upon various conditions, and in variable ratios between fluids. Although the above and other systems are useful in many instances, there remains a need in the art for improved devices that are even more convenient and versatile for simple and rapid application of material to tissue surfaces under a variety of conditions, including a variety of tissue surface conditions.

SUMMARY OF THE INVENTION

The present invention provides device arrangements and methods associated with application of biocompatible material to a surface, such as a tissue surface.

In one aspect, the invention provides a series of devices. One device is constructed and arranged for application of a biocompatible agent to a surface. The device includes a regulation system switchable between a first position arranged to direct delivery of biocompatible agent to the surface via a medical gas at a first medical gas pressure and a second position arranged to direct delivery of biocompatible agent to the surface via a medical gas at a second medical gas pressure. "Direct delivery", in this context, means directing the biocompatible agent to the surface via the medical gas in an amount greater than might drip from the end of a device after a delivery step has been completed. In the above embodiment, the same biocompatible agent can be delivered at both the first and second medical gas pressure, or different biocompatible agents can be delivered under these different conditions.

In another embodiment, a device of the invention, also constructed and arranged for application of biocompatible agent to a surface, includes a housing with a proximal portion for manipulation of the device by a user, a distal portion for delivery of biocompatible agent to the surface, and a central axis along a proximal/distal line. The proximal portion includes switching apparatus external to the housing, operable by a user of the device and including at least three switch positions corresponding to at least three settings of a regulation system associated with the device constructed and arranged for control of delivery of the biocompatible agent to the surface. Switching between any of the at least three switch positions does not result in a change in any switch position along an axis perpendicular to the central axis. This arrangement can allow for simple use of the device in various orientations, by a user, without confusion as to switching position.

In another embodiment, the invention provides a device for application of one or more biocompatible agents to a surface, including apparatus constructed and arranged to deliver at least a first biocompatible agent to the surface, a regulation system having at least a first medical gas pressure setting and a second medical gas pressure setting lower than the first pressure setting, able to deliver medical gas to the surface at least the first pressure and the second pressure, where the regulation system includes at least one preset treatment position delivering the medical gas to the surface at the first pressure in the absence of biocompatible agent.

In another embodiment, a device is provided, constructed and arranged for application of biocompatible agent, including a shaft having a proximal portion that is inflexible under conditions of use, a distal portion that is inelasticly flexible under conditions of use, an inlet associated with the proximal portion connectable to at least one source of biocompatible agent, an outlet associated with the distal portion for release of the biocompatible agent, and a conduit connecting the proximal portion to the outlet.

The invention also provides apparatus including a device constructed and arranged for delivery of a biocompatible material to a tissue surface via pressurized medical gas in a clinical setting. The apparatus includes a pressure regulator adapted to receive a pressurized medical gas, having a preset, non-adjustable pressure setting, and a valved, quick-release connector associated with the regulator, constructed to receive a medical gas line connectable to the device.

In another embodiment, the invention provides a device constructed and arranged for application of a biocompatible agent to a surface, comprising a regulation system switchable to a preset treatment position arranged to direct delivery of a biocompatible agent to the surface via a medical gas at a gas pressure of less than 20 psi.

In another aspect the invention provides a series of methods. One method involves applying a biocompatible agent to a tissue surface by spraying the agent onto the surface via a medical gas pressurized at a first preset gas pressure, and also applying the biocompatible agent to the tissue surface by spraying the agent via a medical gas pressurized at a second preset gas pressure lower than the first preset pressure.

In another embodiment, the invention provides a method of applying a first biocompatible agent to a tissue surface, directing a medical gas, absent any biocompatible agent, at the first biocompatible agent on the surface for a period of time sufficient to alter the first biocompatible agent at the tissue surface, and spraying a second biocompatible agent onto the tissue surface.

The subject matter of this application may involve, in some cases, interrelated products, alternative solutions to a particular problem, and/or a plurality of different uses of a single system or article.

Other advantages, features, and uses of the invention will become apparent from the following detailed description of non-limiting embodiments of the invention when considered in conjunction with the accompanying drawings, which are schematic and which are not intended to be drawn to scale. In the figures, each identical or nearly identical component that is illustrated in various figures typically is represented by a single numeral. For purposes of clarity, not every component is labeled in every figure, nor is every component of each embodiment of the invention shown where illustration is not necessary to allow those of ordinary skill in the art to understand the invention. In cases where the present specification and a document incorporated by reference include conflicting disclosure, the present specification shall control.

DETAILED DESCRIPTION OF THE INVENTION

The following documents are incorporated herein by reference for all purposes relating to components, and arrangement thereof, associated with devices for application of material to a surface, parameters associated with such applications, materials for use in such applications, target surfaces for treatment, and all other disclosure consistent with and complementary to the instant disclosure of the invention. However, where any discrepancy exists between the disclosure herein and any disclosure in any of these references, the description herein controls. These documents are U.S. Pat. Nos. 5,410,016, 5,582,596, 5,665,067, 5,749,968, 5,800,538, 5,749,968, 5,874,500, 5,582,596, 6,121,341, 6,387,977, 6,352,710, 6,217,894 6,051,248, and International Patent Publication Nos. WO 96/29370, WO 99/34833, WO 02/51383, and WO 00/15117.

The present invention involves a device for application of biocompatible material to surfaces using pressurized medical gas. While many useful aspects of the invention will become apparent from the description below, it is initially noted that the device can be used to apply one or any number of biocompatible agents, together or separately, to a surface by spraying them onto the surface using a pressurized medical gas, in combination with lower-pressure gas application, and/or directing pressurized medical gas onto the surface without any biocompatible agent for reasons which will be described below. Lower-pressure application of biocompatible agent in accordance with the invention typically involves controlled dripping, or oozing of biocompatible agent from the device onto a tissue surface.

As will be described below, in one embodiment, the device is specifically designed for application of biocompatible material to a surface in a predetermined sequence of steps involving, for example, a combination of spraying agent, directing pressurized medical gas onto the agent on the surface, spraying a second agent and, optionally, dripping or oozing the second agent onto the surface. In this embodiment the device can be equipped with switching apparatus arranged such that logical, sequential actuation of the switching apparatus results in a predetermined set of treatment steps.

The device can be designed to be operable in any of a variety of orientations relative to a user's hand, and the switching apparatus can be designed such that the logical progression of treatment steps can be followed regardless of orientation, in a logical, simple manner. The switching apparatus is designed, in one embodiment, such that each of a set of preset treatment positions (regulating gas and/or material flow through the device's regulations system) can be selected by the push of a single button.

Figure 10:
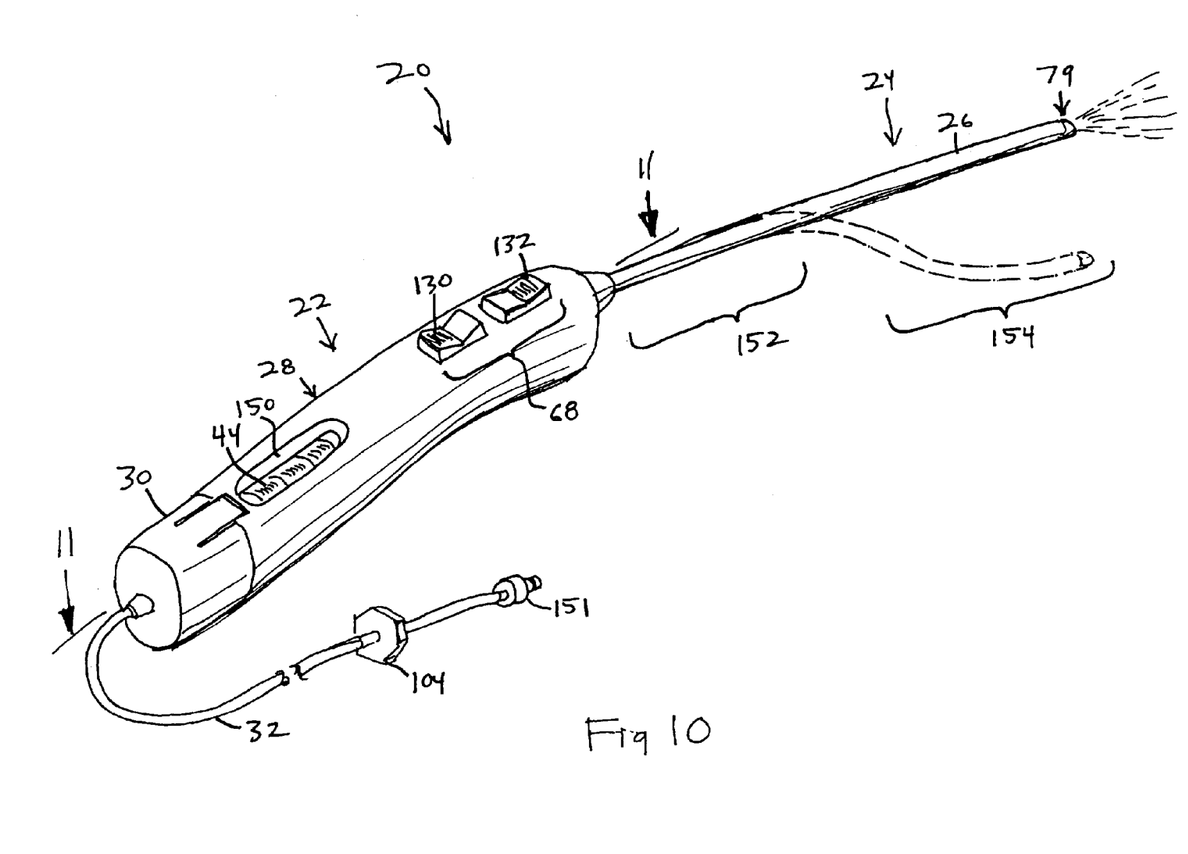
FIG. 10 is a perspective view of the device of FIG. 1 including the devices' housing.

Referring first to FIG. 10, a perspective view of a device 20 according to one embodiment of the invention is shown for reference. The device includes a generally proximal portion 22 operable by a user of the device and a generally distal portion 24, including an application shaft 26, via which material is applied to a surface. Proximal portion 22 includes a housing 28, a portion of which is defined by a removable and replaceable end cap 30 for introduction of and removal of reservoirs of biocompatible material. A gas line 32 delivers pressurized medical gas to the device. Further details relating to FIG. 10 are described below.

Figures 1, 2, 3:
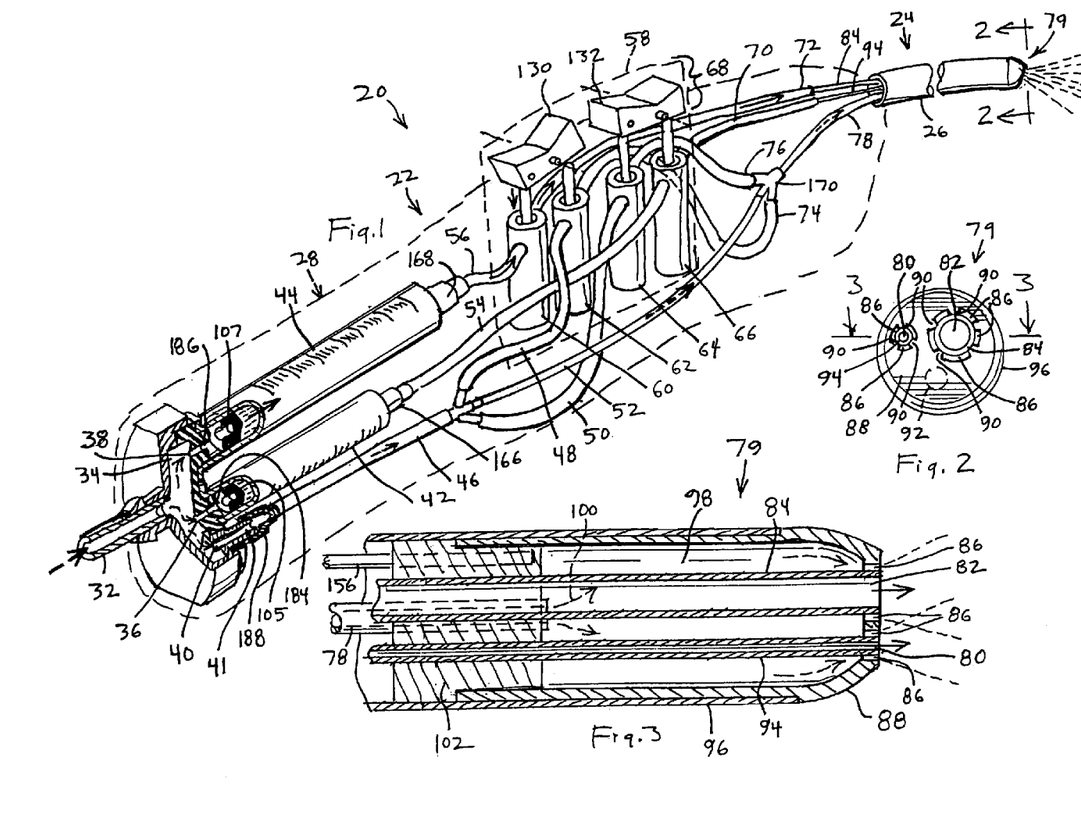
FIG. 1 is a schematic perspective view of a biocompatible agent applicator in accordance with one embodiment of the invention.
FIG. 2 is an end elevational view of the tip of the distal portion of the device of FIG. 1 as seen along line 2—2 of FIG. 1.
FIG. 3 is a cross-sectional plan view of the tip of the device of FIGS. 1 and 2 taken along line 3—3 of FIG. 2.

Referring now to FIG. 1, pathways within the device for storing, receiving, controlling, and delivering biocompatible agents and medical gas are shown in schematic perspective view. Beginning at the proximal end of the proximal portion 22 of the device, gas line 32 delivers a pressurized gas into a manifold 34, which includes three separate outlets 36, 38 and 40. Outlet 36 is in sealed, fluid communication with a first biocompatible agent reservoir 42 and outlet 38 is similarly connected to a second biocompatible agent reservoir 44 in a manner such that the pressurized medical gas exerts pressure upon the contents of each reservoir. Outlet 40 leads into medical gas conduit 46 which branches into conduits 48 and 50 for delivery to regulation system, and bypass conduit 52. Reservoirs 42 and 44 feed into conduits 54 and 56 respectively, which deliver first and second biocompatible agent, respectively, to the regulation system.

Regulation system 58 includes a series of spool valves 60, 62, 64, and 66, actuated by a user of the device via switching apparatus 68, each controlling the flow of a biocompatible agent or a medical gas from a source thereof to the distal portion of the device for controlled application to a surface. Specifically, conduit 70 delivers first biocompatible agent from reservoir 42 (via conduit 54) to the distal portion of the device depending upon the position of spool valve 66. Similarly, conduit 72 delivers second biocompatible agent from reservoir 44 (via conduit 56) depending upon the position of valve 60. Each of conduits 74 and 76 deliver pressurized medical gas to a single, medical gas delivery conduit 78 directed toward the distal portion of the device, from inlet line 32 via conduit 46 and branched conduits 48 and 50 depending upon the position of spool valves 62 and 64, respectively. Gas conduits 46, 48, 50, 74, 76, and 78 are of a dimension, and configured, such that they deliver medical gas at a first, relatively higher pressure to the distal portion of the device. Bypass conduit 52 is sized and/or includes internal constrictions creating back pressure such that when spool valves 62 and 64 prevent delivery of medical gas through conduits 74 and 76, gas only at a second, relatively lower pressure is delivered at conduit 78 to the distal portion of the device.

Accordingly, the regulation system of FIG. 1, in combination with biocompatible agent and gas conduit arrangements, allows delivery of any biocompatible agent provided, and/or high or low pressure medical gas, to the distal portion of the device.

Although two reservoirs of biocompatible agent are shown, it is to be understood that the invention involves use of one or any number of biocompatible agents, and although the arrangement illustrated facilitates delivery of pressurized medical gas at two, preset levels, it is to be understood that any number of pressure levels of medical gas can be provided to the distal portion of the device. Those of ordinary skill in the art, with the benefit of the disclosure herein, would be able to construct and arrange the device for delivery in accordance with any of these options, without undue experimentation. It is to be understood that all of these options are embraced by the present invention, with the invention delineated only by the scope of claims issuing in one or more patents deriving from this application, and their equivalents.

FIG. 2 is an end elevational view of the tip 79, or outlet region of the distal portion of the device as seen along lines 2—2 of FIG. 1. The tip includes two outlets, 80 and 82, fluidly connected to conduits 70 and 72, respectively, for delivery of first biocompatible agent from source 42 and second biocompatible agent from source 44, respectively, from the device. Outlet 82 is defined by the distal tip of a conduit 84, fluidly connected to conduit 72, as described more fully below, and a series of medical gas passages 86 defined by an opening in tip housing 88 larger than the outer circumference of conduit 84, within which conduit 84 is situated (centered, as illustrated) via a series of stand-offs 90. As described in greater detail in connection with FIG. 3, a void space within tip housing 88, within which conduit 84 is positioned, contains pressurized medical gas which can escape through gas passages 86 for delivery of biocompatible material through conduit 82 to a surface. That is, the biocompatible material is introduced into a flowing stream of medical gas surrounding the material, and thereby delivered to the surface. Gas conduit 92, shown in phantom in FIG. 2, delivers pressurized medical gas to this void space. Conduit 92 is the same as, or is fluidly connected to, gas conduit 78.

Outlet 80 is arranged in a manner similar to that of outlet 82, defined by the distal end of a delivery conduit 94, fluidly connected to or the same as conduit 70, and surrounded by gas passages 86. A shaft 96, described more fully below, surrounds the arrangement. Shaft 96 can be the same as shaft 26, or a part of shaft 26, or connected to shaft 26. Shaft 69 is the same as or is connected to shaft 26 previously described in relation to FIG. 1.

As one can observe, the cross-section of outlet 80 is smaller than the cross-section of outlet 82. This is shown in relation to one embodiment in which the viscosity of biocompatible material delivered through outlet 82 is higher than that of material delivered through outlet 80, thus the outlets are sized for optimal flow. In practice, the outlets can take any form or size, easily selected by those of ordinary skill in the art, based upon viscosity and desired flow rate of biocompatible material to be delivered.

In one embodiment, the distalmost end of the device is arranged such that outlets 80 and/or 82 direct sprays of biocompatible agent in a generally conical shape having a central axis aligned with shaft 26. In other embodiments, such as the one illustrated in FIG. 1, the distalmost tip is canted such that the device sprays biocompatible agent at an angle relative to the axis of the shaft. Specifically, in the embodiment illustrated, the distalmost tip is canted downwardly at an angle offset from a plane perpendicular to the axis of the shaft of between 10 and 70 degrees, more typically between 20 and 50 degrees. For example, an angle of 35° or 45° offset downwardly from a plane perpendicular to the shaft can be used.

FIG. 3 is a cross-sectional plan view of tip 78 taken along line 3—3 of FIG. 2. As illustrated in this embodiment, gas conduit 78 supplies pressurized medical gas into a void space 98 (represented by arrows 100) defined by the exteriors of conduits 94 and 84, the interior of tip housing 88, stand-offs 90, and a mounting and sealing member 102 which sealingly resides within shaft 96 and tip housing 88, and within which biocompatible material conduits 84 and 94 and gas conduit 78 are mounted. It can be seen that pressurized medical gas introduced from conduit 78 into void space 98 will continuously escape through air passages 86 surrounding the distal tips of conduits 84 and 94.

Although a variety of conduit arrangements can easily be selected by those of ordinary skill in the art to meet various embodiments of the invention, in the embodiment illustrated, biocompatible material conduits 94 and 84 are not identical to, but fluidly coupled with conduits 70 and 72, respectively (as illustrated in FIG. 1). Conduits 70 and 72 can, for example, be of the same size, with conduit 70 stepped down in cross-section in the form of conduit 94 to an extent greater than conduit 72 in its relation to conduit 74. As mentioned, any adjustment of this type can be made depending upon material viscosity and flow rate requirements.

Figures 4, 5:
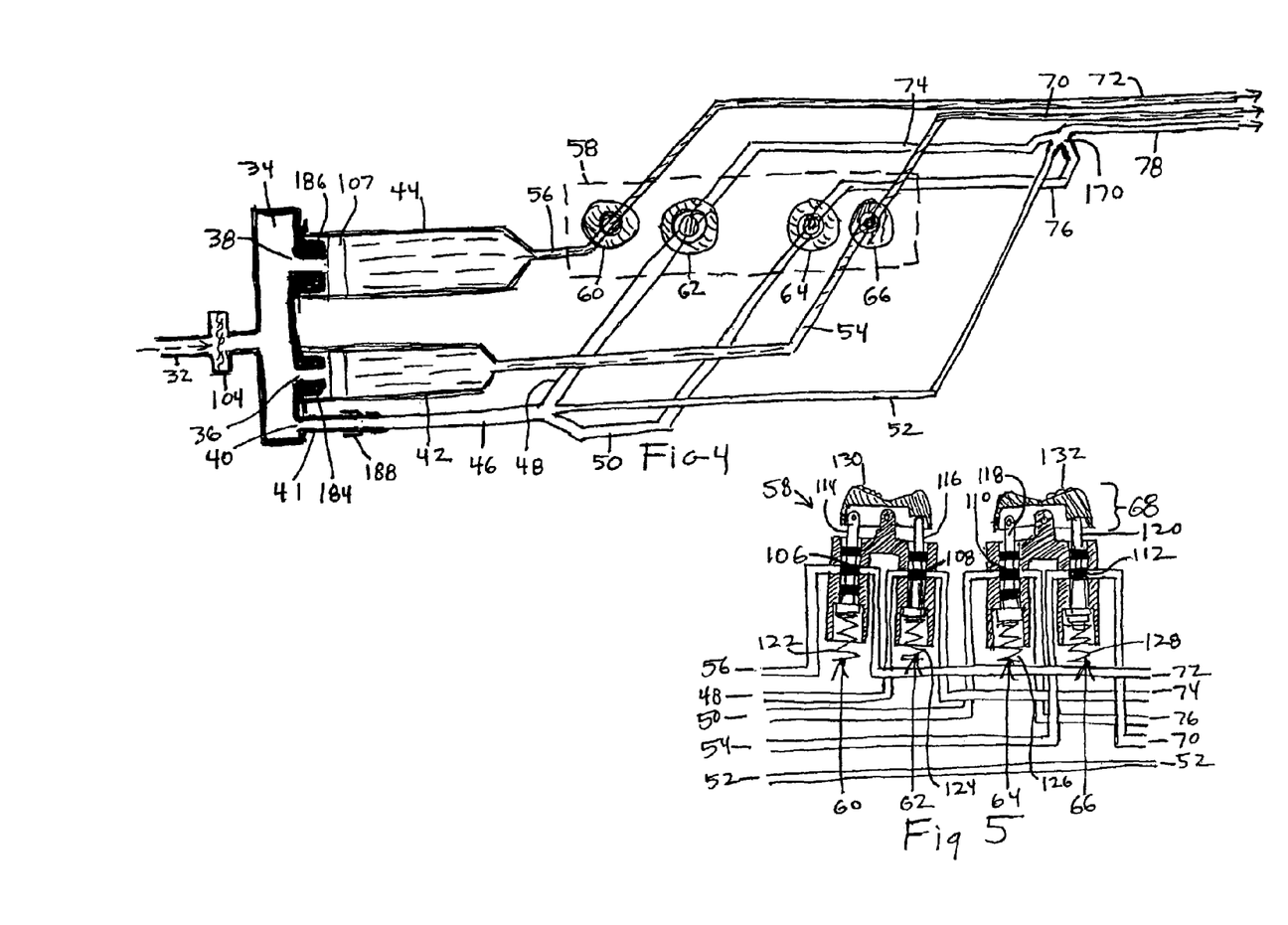
FIG. 4 is a schematic illustration of flow channels for biocompatible agent and medical gas of the device of FIG. 1.
FIG. 5 is a cross-sectional illustration of portions of a regulation system including a series of spool valves of the device of FIG. 1 for controlling flow of biocompatible agent and medical gas, residing in a default position.
Figure 6:
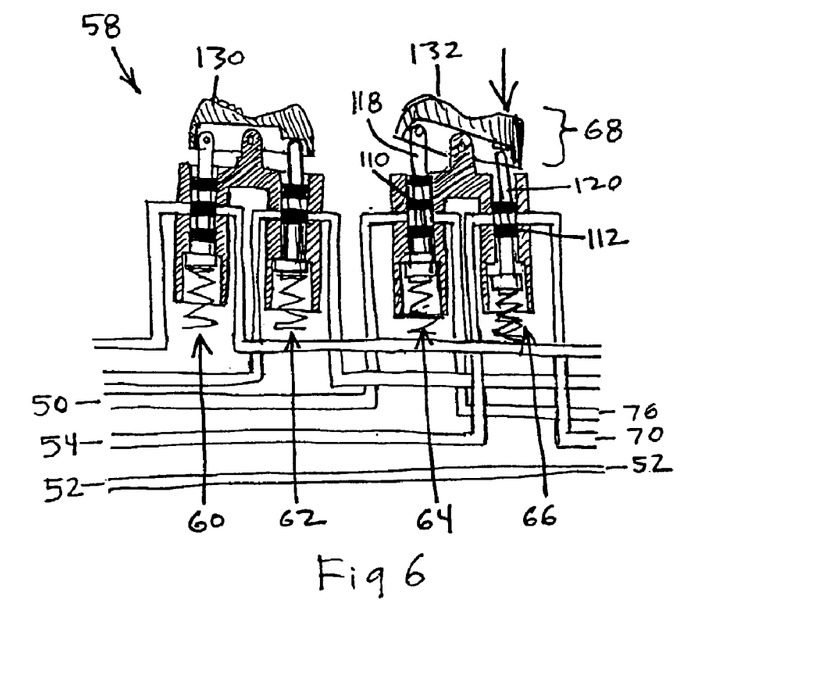
FIG. 6 is a view similar to that of FIG. 5, in which the regulation system is switched into a first preset treatment position.

Referring now to FIG. 4, a further explanation of the fluid flow arrangement described above is provided. At the proximal end of the device, pressurized medical gas is supplied through line 32 and, in the embodiment illustrated, passes through a filter 104 prior to entry into manifold 34. Filter 104 can be provided optionally, depending upon use of the device, and selected by those of ordinary skill in the art for a particular use. In a preferred embodiment the device of the invention is used in a clinical setting for medical treatment which, as those of ordinary skill in the art are aware, requires medical gas substantially free of contaminants. Filter 104 can be selected, optionally in combination with other filters (not shown) for this purpose. Manifold 34 is configured to facilitate the application of pressure, via medical gas from inlet 32, to the contents of first biocompatible agent reservoir 42 and second biocompatible agent reservoir 44, respectively. As illustrated, reservoirs 42 and 44 are syringes, including floating plungers 105 and 107, respectively. Pressure is applied to the proximal sides of the plungers via the medical gas, driving them distally to deliver biocompatible material from the reservoirs if flow from the reservoirs is permitted by the position of the downstream regulation system 58. Manifold 34 also fluidly connects to medical gas conduit 46, which is branched into separate conduits as described in connection with FIG. 1. In the embodiment illustrated, spool valve 60 controls flow of the second biocompatible agent from reservoir 44 to the distal end of the device through conduit 72, valve 62 controls flow of gas at a first pressure to the distal end via conduits 74 and 78, valve 64 similarly controls flow of gas at the first pressure via conduits 76 and 78, and valve 66 controls flow of the first biocompatible material from conduit 42 via conduit 70 to the distal end.

As can be seen, regardless of the position of any of valves 60–66, bypass conduit 52 fluidly connects manifold 34 with the distal end of the device via conduit 78. Thus, as described below, a "default" position of regulation system 58 exists in which each of valves 60–66 is closed but medical gas is delivered to the distal end via conduit 78, and expelled through gas passages 86 (FIG. 3) at a second gas pressure which, in the embodiment illustrated, is lower than the first gas pressure. As illustrated in FIG. 4, the second gas pressure is achieved by using a conduit 52 of smaller cross section than conduits 46, 48, 50, 74, and 76. In another embodiment, conduit 52 is of the same cross-sectional dimension of those conduits, but includes one or more internal constrictions, reducing pressure downstream of conduit 52.

As mentioned above, the embodiments described with respect to the figures represent one set of exemplary embodiments only, and any components, and arrangement of components that satisfy the invention as recited in the claims and equivalents can be selected by those of ordinary skill in the art. For example, although spool valves are illustrated as examples of valves 60–66, other valves can be selected.

Referring now to FIGS. 5–9, operation of spool valves 60–66 is illustrated in partial cross-section. FIG. 13 illustrates this embodiment of a regulation system of the invention in greater detail, in the setting illustrated in FIG. 9, and will be used for more detailed description.

As illustrated in FIG. 5, regulation system 58 is in a default setting in which passage of all biocompatible agent and high-pressure medical gas is prevented by the positions of spool valves 60–66 by seals of rectangular cross-section ("rectangular seals") 106, 108, 110, and 112, respectively, mounted on spools 114, 116, 118, and 120, respectively, of valves 60, 62, 64, and 66. The rectangular seals block passage between upstream conduits and downstream conduits labeled in conjunction with, and described with respect to, FIG. 1 above. Bypass gas conduit 52 remains unrestricted in this default position. Springs 122, 124, 126, and 128, respectively, bias spools 114, 116, 118, and 120 upwardly and, without activation by a user of the device, evenly such that the rectangular seals block passage as illustrated. Activation of rocker buttons 130 and 132 by a user of the device change this arrangement as described below.

FIG. 6 illustrates a first, preset treatment position of the regulation system. As used herein, "preset treatment position" means a setting of the regulation system actuated by a single switching movement by a user of the device. In the embodiment illustrated, each of rocker buttons 130 and 132 includes two, mutually exclusive switching positions, thus it can be seen that switching mechanism 68 defined by these rocker buttons and their connection to the spool valves defines four, separate depressed button positions. That is, the system includes four preset treatment positions each requiring the user to perform one switching step, namely, depression of a button.

The first preset treatment position, illustrated in FIG. 6, involves depression of the distal button region of rocker button 132, illustrated by the arrow. In this position, spool 120 is driven downwardly within its cylinder, displacing rectangular seal 112 and allowing fluid connection between conduit 54 and conduit 70, allowing first biocompatible material to be driven from reservoir 42 toward the distal end of the device. Simultaneously, spool 118 is drawn upwardly in its cylinder, displacing rectangular seal 110 and connecting conduits 50 and 76, allowing high-pressure medical gas to be driven toward the distal end of the device. Referring now to FIGS. 2 and 3, this causes first biocompatible material to be expelled through outlet 80 and, simultaneously, high-pressure medical gas is introduced into void space 98 from conduit 78 to which conduit 76 leads. High-pressure gas within void space 98 escapes through gas passages 86 surrounding outlet 80, carrying the first biocompatible agents to a surface. In one embodiment, at this medical gas pressure biocompatible material expelled from outlet 80 is drawn into a stream of the medical gas flowing at a rate sufficient to spray the biocompatible material at the surface. Simultaneously, as in all other settings, lower-pressure medical gas is delivered via conduit 52, bypassing the spool valves and delivered constantly to void space 98 at the distal portion of the device.

Referring now to FIG. 7, a second preset treatment position of the regulation system is shown in which the proximal section of rocker button 132 is depressed, as shown by the arrow. In this arrangement spool 118 is driven downwardly, displacing rectangular seal 110 within the cylinder in which it resides, allowing connection between conduits 50 and 76, driving high-pressure medical gas to the distal end of the device. This result also is achieved in the first preset treatment position illustrated in FIG. 6. However, in the second preset treatment position of FIG. 6, rectangular seal 112 is not displaced as spool 120 is not drawn upwardly by upward movement of the distal portion of rocker button 132, and is prevented from upward movement by the arrangement of the spool and its housing, as illustrated. In the second preset treatment position, high-pressure medical gas escapes through all available orifices of the distal end of the device (passages 86) without any biocompatible agent, the utility of which will be described below.

Figure 8:
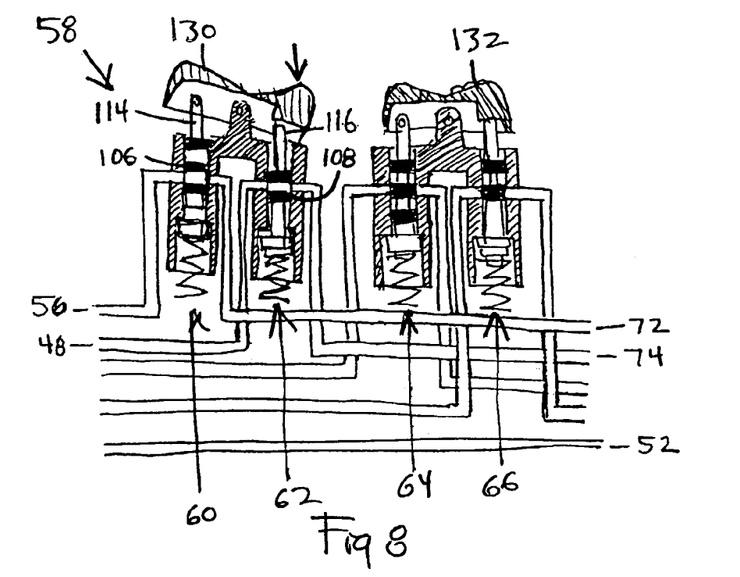
FIG. 8 is a view similar to that of FIG. 5, in which the regulation system is switched into a third preset treatment position.

Referring to FIG. 8, a third preset treatment position is illustrated in which the distal portion of rocker button 130 is depressed as illustrated by the arrow. In this arrangement spool 116 is driven downwardly within its cylinder, displacing rectangular seal 108 which allows connection between conduit 48 and conduit 74, delivering high-pressure medical gas to void space 98. Simultaneously spool 114 is drawn upwardly, displacing seal 106 in the cylinder in which it resides, thereby fluidly connecting conduits 56 and 72 and allowing delivery of the second biocompatible material from reservoir 44 to the distal end of the device where it is released at outlet 82. In this high-gas-pressure arrangement, conditions can be selected such that the biocompatible material is sprayed onto the surface.

Figure 9:
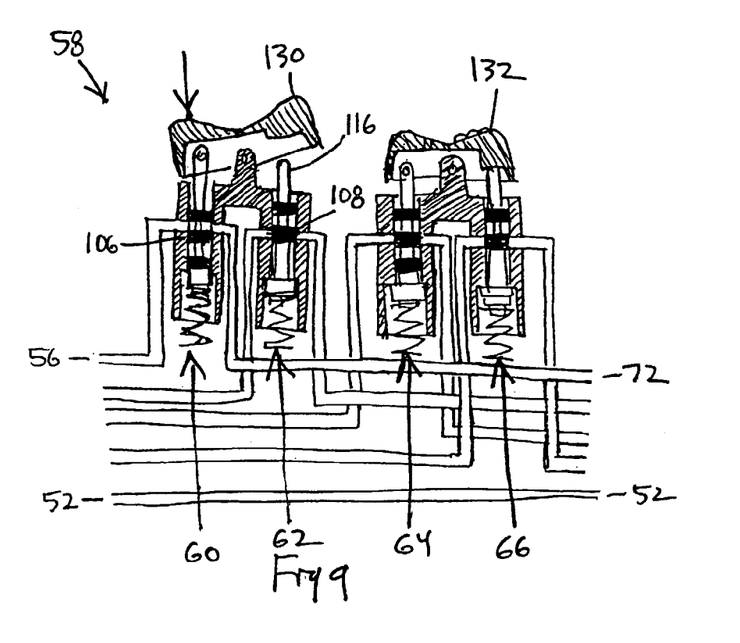
FIG. 9 is view similar to that of FIG. 5, in which the regulation system is switched into a fourth preset treatment position.

Referring now to FIG. 9, a fourth preset treatment position is illustrated in which the proximal section of rocker button 130 is depressed by a user, driving spool 114 downwardly and displacing seal 106 to fluidly connect conduits 56 and 72, delivering second biocompatible material from reservoir 44 to be expelled through outlet 82, in an arrangement similar to that of FIG. 8. However, spool 116 need not travel upwardly in its cylinder, and is blocked from doing so by the arrangement of the spool to the cylinder within which it resides, as illustrated. Thus, seal 108 blocks passage of high-pressure gas to the distal end of the device and the second biocompatible material is expelled from outlet 82 in combination only with low-pressure medical gas delivered into void space 98 via bypass conduit 52.

Figure 13:
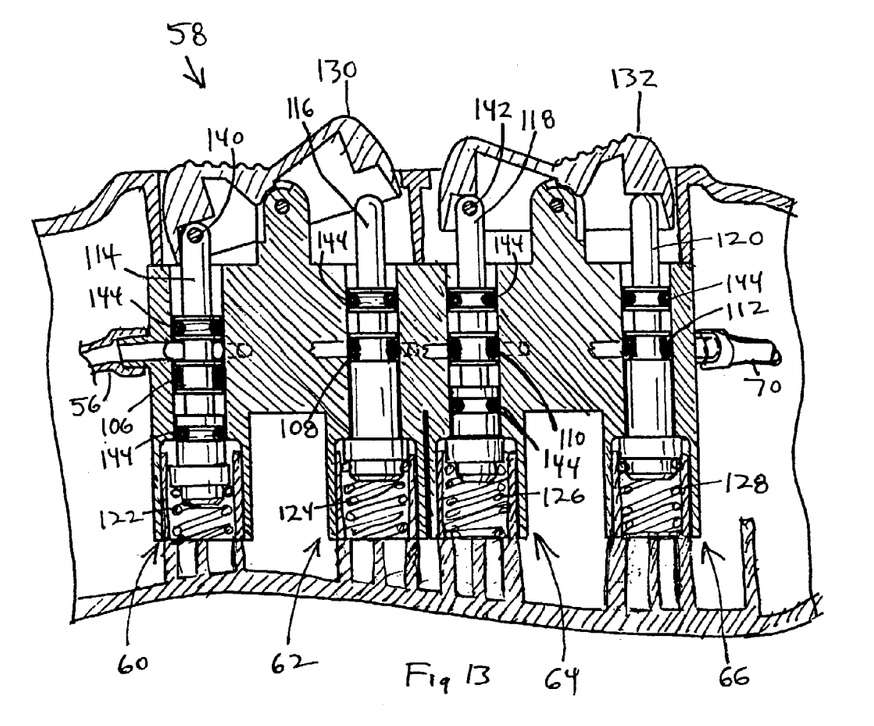
FIG. 13 is a side, cross-sectional view of the regulation system of FIG. 5, taken along line 13—13 of FIG. 11 shown in the fourth preset treatment position of FIG. 9, but in greater detail.

Referring now to FIG. 13, regulation system 58 is shown in greater detail, switched into the fourth preset treatment position illustrated in FIG. 9. As can be seen, spools 114 and 118 are both depressed downwardly and drawn upwardly depending upon the position of rocker buttons 130 or 132, respectively, by their connection to the rocker buttons via cross pins 140 and 142, respectively. Spools 116 and 120, however, can be depressed downwardly by action of rocker buttons 130 or 132, respectively, but are not operably connected to the rocker buttons to be drawn upwardly, and are prevented from being drawn upwardly by the arrangement of the spool valves. Spools 114 and 118 are biased upwardly by action of springs 122 and 126, respectively, urged against intermediate, upward-biasing members which butt against the bottom of the spools. The upward-biasing members are limited in their upward travel by shoulders defining the bottom ends of cylinders within which the spools ride. When spools 114 and 118 are drawn upwardly (i.e. in FIGS. 6 and 8), the spools separate from and ride upwardly within their cylinders away from these upward-biasing members, which remain blocked from upward movement by the shoulders defined by the bottom end of the cylinders.

As can be seen, a series of o-rings 144 are provided on the spools such that when rectangular seals 106, 108, 110, or 112 are displaced from their position blocking upstream and downstream conduit connection, an intermediary conduit is defined between the rectangular seal and an o-ring that connects an upstream with a downstream conduit. The rectangular seals and o-rings ride in bosses. It can be seen that spools 114 and 118 require two o-rings for definition of two separate intermediary conduits, while spools 116 and 120 require only one.

Figure 7:
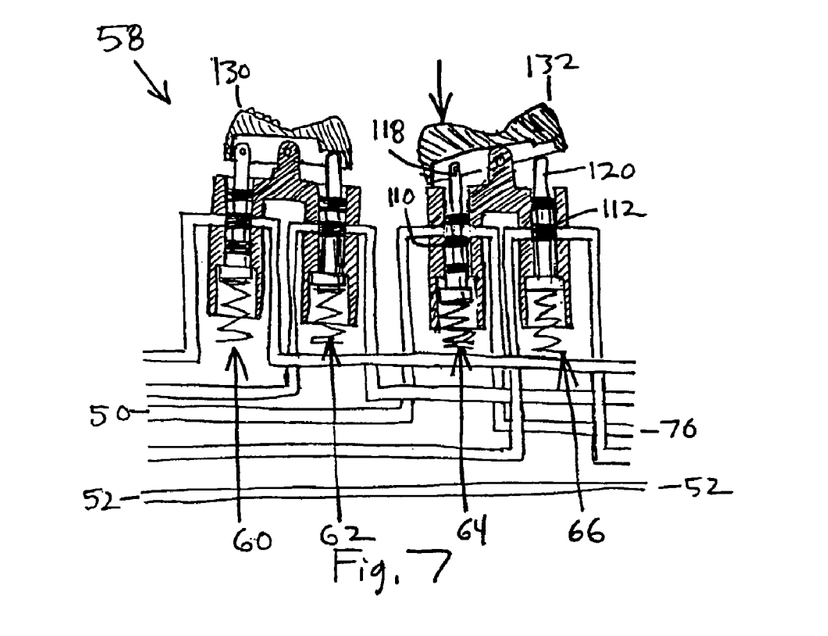
FIG. 7 is a view similar to that of FIG. 5, in which the regulation system is switched into a second preset treatment position.

As can be seen, the regulation system is interconnected with the switching apparatus such that when the device is activated in any preset treatment position (not including the default position), at least one other preset position is inactivatable. For example, in the first preset treatment position of FIG. 6 the second preset treatment position of FIG. 7 is unachievable. Similarly, the third and fourth preset treatment positions of FIGS. 8 and 9, respectively, are mutually exclusive. Thus, in the first preset treatment position the second preset treatment position is inactivatable, and vice versa, and in the third preset treatment position the fourth preset treatment position is inactivatable, and vice versa. This leads to simplicity of use of the device by reducing options. The invention can be practiced without any of this mutual exclusivity between switching positions corresponding to preset treatment positions, or can be arranged for complete mutual exclusivity. That is, any number of preset treatment positions can be provided, any number of which are mutually exclusive with respect to any others. I.e., any number of preset treatment positions can be provided, none of which can be activated if any other is activated.

Referring now to FIG. 10, a perspective view of one embodiment of device 20 is illustrated. In the embodiment illustrated, a housing 28 encloses regulation system 58, with switching apparatus 68, defined by rocker buttons 130 and 132, exposed for activation by a user. Housing 28 encloses biocompatible agent reservoirs 42 and 44, although a window 150 is provided in the embodiment illustrated, so that when a transparent reservoir 44 or 42 is used, the user can view the amount of biocompatible agent within the reservoir. The device can include a window or be free of such a window, and in one embodiment a window is provided on both the top of the device (as shown) and on the bottom of the device (hidden) so that the content of both reservoirs can be evaluated. Inlet line 32 connects to an end cap 30 which forms part of housing 128 and connects thereto. The inlet line includes an end 151 which, in one embodiment, can connect to a valved, quick-release connector associated with a pressure regulator. In the arrangement illustrated, the device is constructed such that a single medical gas is introduced into manifold 34, driving all aspects of the device requiring gas, with tubing and constrictions selected to deliver predetermined gas pressures, resulting in predetermined flow rates, throughout the device. Accordingly, a user of the device need not select from among different gas sources and different gas pressures, but can use a single gas source at a single gas pressure at which the device is designed to operate. Accordingly, one aspect of the invention includes device 20 in combination with a pressure regulator adapted to receive a pressurized medical gas, where the pressure regulator has a preset, non-adjustable pressure setting. A valved, quick-release connector can be associated with the regulator, constructed to receive gas conduit 32, via connection at 151. Suitable gas pressures are described below.

In one embodiment, shaft 26 includes a proximal portion 152 that is inflexible under conditions of use and a distal portion 154 that is inelastically flexible under conditions of use. The distal portion 154 also can be elastically flexible under conditions of use in some embodiments. By "inflexible under conditions of use" is meant that the proximal end of the shaft cannot be readily bent by a user of the device.

If a user of the device were to apply bending pressure to the proximal end of the device, he or she, if of ordinary skill in the art and familiar with such devices, would immediately recognize the proximal portion was not designed for bending by a user. "Flexible under conditions of use" means that a user of ordinary skill, applying bending pressure to the distal end, would find that it bends under acceptable pressures. Moreover, in one set of embodiments, the distal portion is flexible enough that when urged against a tissue surface of a patient using a force acceptable to that tissue, the distal portion can be bent. This allows bending of the distal portion during use without direct manipulation by a user. "Inelastically flexible" means that when the distal portion is bent, it remains in its bent configuration unless further force is applied. Thus, the distal portion can be bent by a user into a configuration particularly suitable for a particular treatment arrangement, and will remain in that configuration until returned to its original position. To achieve this, in one embodiment the proximal portion of the shaft includes an outer, relatively stiff stainless-steel tube optionally covered by medically-acceptable plastic, and the distal portion it is a medically-acceptable tube including a stainless-steel stiffener wire which can be inelastically bent by a user. As one example, a stiffener wire 156 is shown in at least FIGS. 3, 11, and 12.

As also can be seen with reference to FIG. 10, the device is arranged such that simple, logical progression through preset treatment positions can be accomplished by a user of the device and easily reproduced regardless of the orientation of the device. In the embodiment illustrated, first, second, third, and fourth preset treatment positions are achieved by sequential depression of the four button positions defined by rocker buttons 130 and 132 starting from the distalmost rocker button position and moving toward the most proximal. That is, distal portion of rocker button 132 is depressed, followed by proximal portion of that button, followed by depression of distal portion of rocker button 130, followed by depression of the proximal portion of that button. Referring to FIG. 10, when a user of the device holds housing 28 in his or her outstretched hand with the distal portion facing away from him or her, the user can simply actuate these sequence of button positions with his or her thumb. By reversing the orientation of the device in the hand such that the proximal portion faces the user, these button positions can easily be similarly actuated in the same sequence. The user need only pay attention to the fact that button positions should be actuated from the distal end of the rocker buttons toward the proximal end (of course, the buttons can be arranged for actuation in the opposite direction). This simple arrangement is achieved by providing the device with a central axis running from the proximal end of the device toward the distal end. Switching apparatus 68 is arranged along this axis such that switching between any of the switched positions does not result in a change of any switch position along an axis perpendicular to the central axis. Although four switch positions are shown (proximal or distal depression of each rocker button), any number of switch positions can be provided and can take advantage of this arrangement, for example, two, three, four, five, six, at least eight, or at least ten or more switch positions. In this arrangement, the switching apparatus falls within a plane whereupon switching between any of the at least three switch positions does not result in movement of any of the switching apparatus relative to the plane. In the arrangement illustrated, the plane bisects rocker buttons 130 and 132. Thus, the user of the device need not pay any attention to left/right orientation, which of course would reverse upon reversal of orientation of the device relative to the user. Proximal/distal orientation of switching positions of the device does not change relative to the device itself, which is much easier to monitor.

Although not illustrated in FIG. 10, housing 28 can include texturing for easier gripping by a user of the device. Typically, texturing is found on the bottom portion of housing 128 (from the perspective illustrated in FIG. 10). In one embodiment housing 128 is a single, molded unit or a two-piece molded unit that fits together, with openings for connection of shaft 26 and protrusion of buttons 130 and 132. Windows 150, 153 can also be provided.

A variety of biocompatible materials can be delivered using the device of the invention. As mentioned, one biocompatible material or any number of biocompatible materials can be used, with the device configured to accept different numbers of materials. As illustrated, housing 28 is constructed to mount insertable and removable reservoirs of biocompatible material 42 and 44, in the form of syringes. However, built-in reservoirs can be provided. Alternatively, the device can be constructed so as not to receive reservoirs of biocompatible material, but to include inlet ports for connection to conduits that supply biocompatible material to the device.

Any suitable biocompatible material can be selected, such as those described in any of the above-identified patents or international patent publications incorporated by reference. Where a two-component liquid tissue coating is used, in one embodiment, the first biocompatible material (provided in reservoir 42) is a "primer" or "photoinitiator" and the second biocompatible material (provided in reservoir 44) is a "sealant". As used herein, "primer" is a material that can improve adhesion of another material, or can assist in changing the form of another material in some way. For example, a "photoinitiator" is a material reactive upon exposure to electromagnetic radiation, such as visible light, to cause another material to begin to polymerize or to enhance polymerization of another material. Thus, a photoinitiator can be applied to a surface followed by application of a polymerizable material over the photoinitiator. Exposure of this arrangement to electromagnetic radiation matched for activation with the photoinitiator can cause polymerization of the polymerizable material beginning at the surface and extending away from the surface. As such, adhesion to the surface can be enhanced, and the thickness of the resulting polymer layer on the surface can be controlled by control of the time during which the material is exposed to the radiation. Since the material polymerizes in a direction away from the surface, and may be photoactively-driven depending upon selection of material, when the radiation source is removed, polymerization ends and excess material can be washed away leaving a medically-acceptable coating of material at a predetermined thickness. One preferred material is a "primer" and "sealant" combination sold under the trademark FocalSeal® under the product designation FL8000 Material Kit by Genzyme Biosurgery, One Kendall Square, Cambridge, Mass. 02139.

Other materials are suitable as well. Any two-component liquid tissue coating can be dispensed with the device, including those described in U.S. Pat. Nos. 5,749,968 and 5,800,373 and international patent publication no. WO 96/29370, which are hereby incorporated by reference. These include the free-radical polymerizable coating described above, for which the alternating application method is preferred. Two-component systems can also be made from components A containing amine or hydroxyl groups and components B containing isocyanate, dialdehyde, polyaldehyde, polyphenol or epoxy groups, in which A and B react to form covalent crosslinks on contact. Catalysts or accelerators may be included in the formulation as required. Any of the biocompatible materials used in the invention can be all-natural (i.e., including no synthetic materials; no materials synthesized by human-directed chemical synthesis), or all synthetic materials, or any combination. In one embodiment, all biocompatible materials are synthetic.

Other reactive coatings are formed by the coacervation of oppositely charged polymers. In this case A is a polyanion and B is a polycation; for example, A could be alginate and B polylysine or chitosan. In a variant of this, certain ionic polymers, such as alginate, can be gelled by the addition of specific small molecules or ions, such as calcium ions. Then A could be alginate and B a solution of calcium ions.

Either or both of the reactive components A and B may comprise a polymeric backbone. The backbone may be made of any polymer which is acceptable in the particular medical use. Such polymers are preferably biocompatible, wherein no sustained or excalating inflammatory response is elicited. In most cases, it is preferably that the polymer be biodegradable, or that the polymer be linked to the coating by biodegradable linkages, and itself be secreted from the body. Biodegradable linkages include esters, especially of hydroxy acids; amides; anhydrides; and other labile linkages known in the art. Synthetic polymers are preferred. However, the polymer may comprise a natural polymer, such as fibrinogen, or a synthetic derivative of a natural polymer, such as an acrylated polysaccharide. A typical preferred polymer mixture will be predominantly synthetic, but make contain some proportion of unmodified natural polymers, such a 20%, while being described as predominantly synthetic. Natural polymers which have been chemically altered are not considered to be identical with natural polymers. Natural polymers included for their effects as biologically active materials are not considered to be part of the coating polymers unless otherwise stated.

Still other reactive coatings are formed by the action of enzymes on substrates. Fibrin sealant is a well-known example of such a coating. Other reactive coatings can be formed by the binding of the members of a binding pair. A well-known pair, suitable for creating coatings, is biotin conjugated to a polymer, plus the protein avidin, optionally conjugated to a polymer. Similarly, the binding of antibodies to polyvalent antigens can form a coating.

In addition to the reactive components, other materials may be incorporated into the coating during its application. These include biologically active molecules, including conventional small-molecule organic drugs, proteins and peptides, nucleic acids, polysaccharides and inorganic materials. The proteins can be, among others, enzymes, growth factors, growth inhibitors, antibodies, cell attachment modulators, and immune system modulators.

Those of ordinary skill in the art would recognize the meaning of the word "biocompatible material". These materials are suitable for use in connection with a living patient, for use internally and/or externally. These materials also can be used to coat clinical components for use in a medical setting. For example, the sprayer of the invention can be used to apply a biocompatible material to an object such as an implant, prosthesis, or the like which is to be inserted into a patient, although the device might more commonly be used for application of material directly to a tissue surface of a living patient. Once class of biocompatible materials are sterilizable materials or materials that are provided in sterile form.

The device may be used to create coatings useful in the treatment of any medical condition where such a coating is useful. Such conditions include, without limitation: prevention of adhesions, sealing of leaks of bodily fluids or air, sealing of anastamoses, staple lines and suture lines, coating of surfaces to protect them, for example, from friction or exposure to air, adhering tissue together or adhering tissue to an implant, formation of implants for delivery of drugs or cells, or for mechanical support, and dressing of external and internal wounds.

Where a primer/sealant arrangement is used as described above, its operation in connection with device 28 is as follows. Primer can be supplied in reservoir 42 with sealant supplied in reservoir 44. As will be described more fully below with reference to FIGS. 14 and 15, use of the device can simply involve removal of end portion 30, insertion of reservoirs 44 and 42 into the device, closure of the housing by connection of end portion 30 via a snap-fit connection, connection of gas conduit 32 to a source of medical gas, and operation of rocker buttons 130 and 132. Once connected, initially low-pressure gas flows continuously through passages 86 at the tip of the device. Upon depression of the distal portion of rocker button 132, primer is delivered through outlet 80 under higher gas pressure, preferably selected to spray the primer against the target surface. Once sufficient primer has been applied, proximal portion of rocker button 132 is depressed, resulting in high-pressure gas expelled through gas passages 86 at the tip of the device in the absence of any biocompatible material. This can be directed at the previously-applied primer, driving it into voids within the tissue surface. Then, the distal portion of rocker button 130 is depressed, causing sealant to be expelled through outlet 82 at the distal tip, along with high-pressure gas through gas passages 86, spraying the sealant onto the tissue surface, typically directly over the primer. Finally, the proximal portion of rocker button 130 can be depressed, resulting in the release of sealant from outlet 80 without high-pressure gas release. Lower-pressure gas supplied into void 98 via bypass conduit 52 typically is of a pressure selected to cause sealant to be dripped, or oozed onto the surface, and potentially at a high enough pressure to slightly direct application of the sealant on the surface. However, the low-pressure delivery does not result in spraying of the sealant onto the surface in one set of embodiments. This can be useful in a situation where sealant, sprayed from the device, does not evenly or adequately coat portions of the tissue surface. For example, when sealant is sprayed at a tissue surface including a protrusion facing the device, sealant might be applied adequately to portions of the surface except the most outward-facing portion, or apex, of the protrusion. In such a case, the proximal portion of rocker button 130 can be depressed to express a volume of sealant directly onto the portion of the surface requiring more sealant.

Although not illustrated, an emitter of electromagnetic radiation, selected to polymerize the photoinitiator/sealant combination, can be provided in combination with the device. In one embodiment, an emitter is mounted in association with the device, for example, mounted at the tip of the device, and fed by an electrical lead, optical fiber, or the like, from a connection at the proximal end of the device which itself is connected to a source of electromagnetic radiation or other energy. Activation of this emitter can then cause polymerization. In another embodiment, a separate emitter of electromagnetic radiation, not connected to device 20, as used. One example of such an emitter is an LW1000 Light Wand sold by Genzyme Biosurgery. Exposure of the primer and sealant, on the surface, to appropriate electromagnetic radiation, causes polymerization of the sealant against the tissue surface with polymerization extending outwardly therefrom. When primer has been driven into the tissue surface via the second preset treatment position (application of high-pressure gas only), adhesion of sealant to tissue can be enhanced.

As mentioned, gas pressures and biocompatible materials can be selected in combination to provide any arrangement of spraying, dripping, and the like of material onto a tissue surface. In one embodiment, the first medical gas pressure of the invention is at least 25 psi, or at least 30 psi or 35 psi input through conduit 32 and, assuming negligible loss through the system, approximately 25, 30, or 35 psi, respectively, applied within void space 98 in the first, second, and third present treatment positions. In one embodiment, conduit 52 steps pressure down to approximately 25 psi or below, in one embodiment between 20 and 25 psi, and in another embodiment less than 20 psi, less than 15 psi, or less than 10 psi with gas at this pressure being continuously supplied to void space 98.

Figure 11:
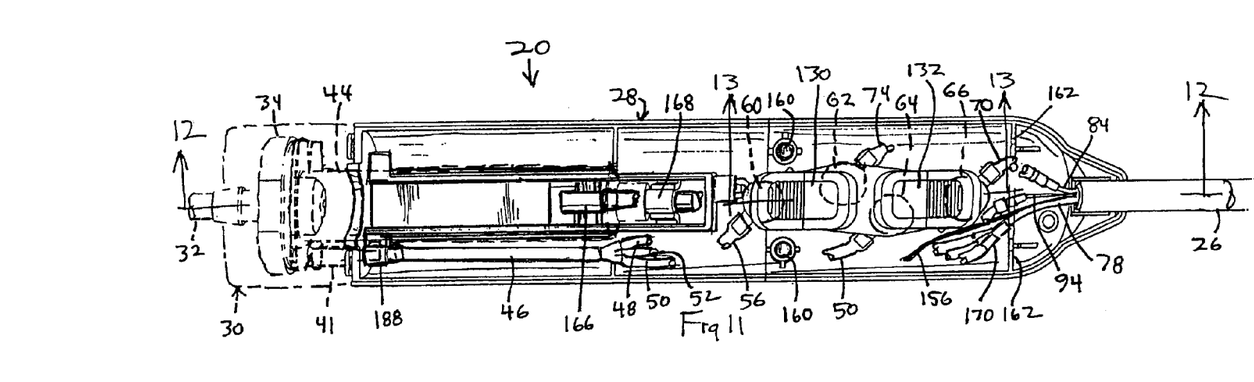
FIG. 11 is a top plan view of the device of the above figures as seen along line 11—11 of FIG. 10 with the cover of the device removed, tubing broken away for clarity, and biocompatible agent reservoirs in the form of syringes shown in phantom for clarity.
Figure 12:
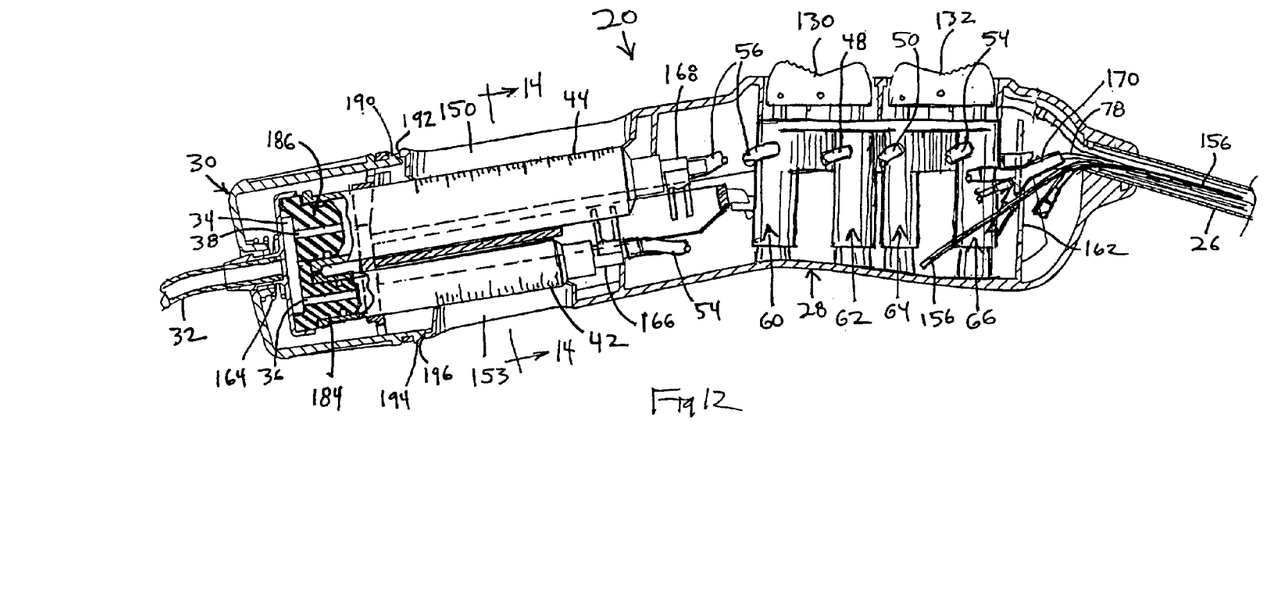
FIG. 12 is a side cross-sectional view of the device of the above figures taken along line 12—12 of FIG. 11 with some components broken away for clarity.

Referring now to FIGS. 11 and 12, certain aspects of device 20 are illustrated in greater detail (or less detail where this adds clarity). FIG. 11 is a top plan view of the device as seen along line 11—11 of FIG. 10 but with the proximal end cap and cover of the device removed and tubing broken away, and biocompatible material reservoirs (syringes) shown in phantom for clarity. Most components are described above. FIG. 11 also shows sockets 160, on the bottom portion of the housing, which mate with posts on the housing cover. Walls 162 includes holes which hooks on the housing cover engage. Of course, a variety of arrangements can be used to connect components of the invention.

FIG. 12 is a side, cross-sectional view through lines 12—12 of FIG. 11, with reservoirs and the regulation system shown in plan view, and some components removed for clarity. A spring 164 is shown, which loads floating manifold 34 against agent reservoirs and the bypass conduit. In one embodiment, the device includes Luer receptacles 166 and 168, respectively, to receive biocompatible agent reservoirs 42 and 44, when they take the form of syringes. In one embodiment these Luer fittings are friction-fit, into which the syringes do not screw. A "Y" connector 170 is shown which joins gas conduits 52, 74, and 76, leading them into gas conduits 78.

Figure 14:
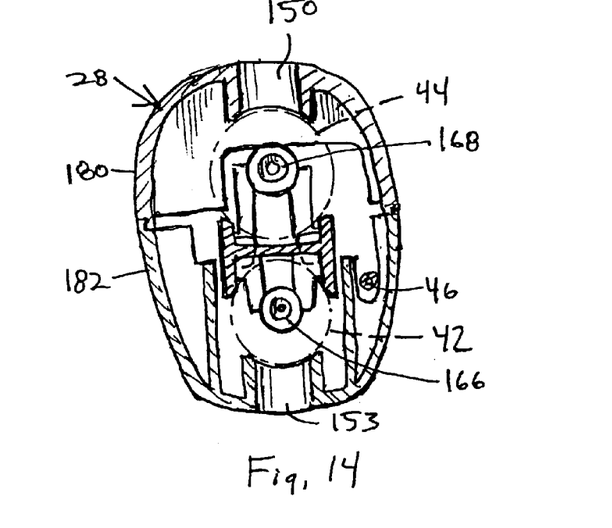
FIG. 14 is a cross-sectional end view taken along line 14—14 of FIG. 12, with biocompatible agent reservoirs shown in phantom for clarity.
Figure 15:
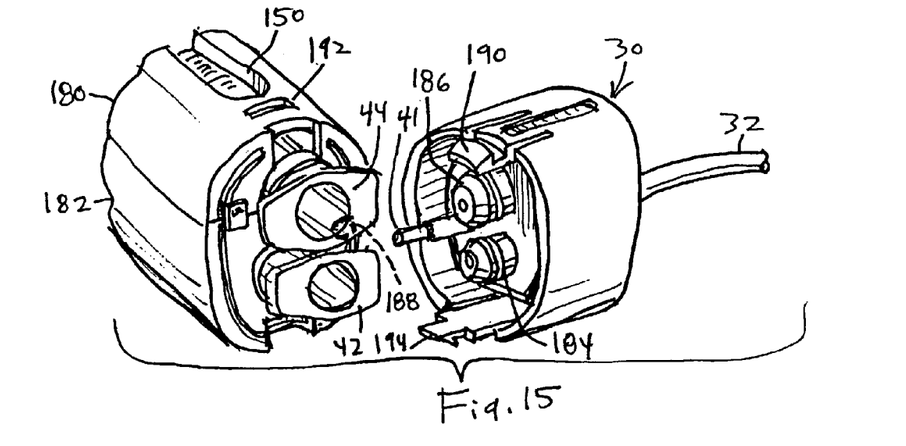
FIG. 15 is an exploded perspective view of a section of the proximal portion of the device of the above figures, with an end cap of the device removed.

Referring now to FIGS. 14 and 15, the proximal portion including manifold and reservoirs, and their housing, is illustrated in greater detail. FIG. 14 is a cross-sectional end view taken along line 14—14 of FIG. 12, with reservoirs 42 and 44 shown in phantom for clarity. The housing includes a top portion 180 and a bottom portion 182, in the embodiment illustrated, and compartments into which the reservoirs can be mounted. Window 150 is shown in FIG. 14, as well as an opposite window 153 for viewing the contents of first biocompatible agent reservoir 42.

FIG. 15 is an exploded perspective view of the proximal end of the device with end cap 30 removed. Reservoirs 42 and 44 in the form of syringes are shown mounted in the device. End cap 30 shows connection downstream of manifold 34, coupling to the reservoirs end gas conduit 46. As illustrated, a male member 184 mates with a syringe defining reservoir 42 and a similar member 186 mates with a syringe defining reservoir 44. These members sealingly engage the syringes by insertion into the syringes, and include O-rings for sealing engagement within the syringes. A connector 41 sealingly engages a receptacle 188 (FIG. 1) connecting the manifold to gas conduit 46. Hook 190 in the end cap snaps within a hole 192 in the mating portion of the housing and hook 194 similarly engages another hole 196 in the housing, shown in FIG. 12.

As can be seen in FIGS. 14 and 15, a single, molded unit, optionally a multi-part unit fitted together, receives reservoirs 42 and 44 easily, with easy snap-fit connection to a driving source of medical gas. In use, the device is simply loaded with reservoirs, the end cap is snapped in place, connection is made to a source of medical gas, and the device is ready for use. Reservoirs can be replaced during use by simple removal of the end cap, replacement, and reconnection of the end cap.

Components of the device can be fabricated from any suitable materials, preferably medically-acceptable, sterilizable materials. In one embodiment, the entire device is a one-use, disposable device. Those of ordinary skill in the art of medical devices will readily recognize suitable materials for such uses, thus not every component of the invention will be described in terms of its composition. Generally, standard PVC medical tubing can be used as conduits. The housing and other supporting structures can be injection molded from ABS polymer, or acrylic polymer where transparency is desired (e.g. windows 150 and 153 where they are covered with polymer, rather than simply being open spaces). PEBAX™ tubes can be selected for distalmost conduits 84 and 94 for delivery of biocompatible material. Shaft 26 can be a stainless steel tube coated or covered with urethane material. Elastomeric components, such as inserts, o-rings, seals, syringe gaskets, and the like, can be made of EPDM. Spool valves are typically made of elastic molded or elastomeric components with the spools themselves being made of aluminum.

While several embodiments of the invention have been described and illustrated herein, those of ordinary skill in the art will readily envision a variety of other means and structures for performing the functions and/or obtaining the results or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, if such features, systems, materials and/or methods are not mutually inconsistent, is included within the scope of the present invention.

In the claims (as well as in the specification above), all transitional phrases such as "comprising", "including", "carrying", "having", "containing", "involving", "composed of", "made of", "formed of" and the like are to be understood to be open-ended, i.e. to mean including but not limited to. Only the transitional phrases "consisting of" and "consisting essentially of" shall be closed or semi-closed transitional phrases, respectively, as set forth in the United States Patent Office Manual of Patent Examining Procedures, section 2111.03.

What is claimed is:

1. A device constructed and arranged for application of a biocompatible agent to a surface, comprising a regulation system switchable between a first position arranged to direct delivery of a biocompatible agent to the surface via a medical gas at a first medical gas pressure, and a second position arranged to direct delivery of the biocompatible agent to the surface via a medical gas at a second medical gas pressure;

further comprising a first biocompatible agent conduit connectable to a source of a first biocompatible agent, the conduit including a first biocompatible agent outlet adapted to emit the first biocompatible agent for delivery to the surface, and a gas conduit connectable to a source of a pressurized medical gas and having an outlet adapted to emit pressurized medical gas in an orientation carrying the first biocompatible agent from the first biocompatible agent outlet to the surface;

further comprising a second biocompatible agent conduit connectable to a surface of a second biocompatible agent, the second conduit including a second biocompatible agent outlet adapted to emit the second biocompatible agent;

wherein the second biocompatible agent outlet is positioned to emit the second biocompatible agent in relation to a pressurized medical gas outlet in an orientation carrying the second biocompatible agent from the second biocompatible agent outlet to the surface;

further comprising a regulation system having a first preset treatment position arranged to direct delivery of the first biocompatible agent to the surface via a medical gas at a first medical gas pressure, and a second preset treatment position arranged to direct delivery of the medical gas to the surface in the absence of any biocompatible agent;

the regulation system further including a third preset treatment position arranged to direct delivery of the second biocompatible agent to the surface via a medical gas at the first medical gas pressure;

the regulation system further including a fourth preset treatment position arranged to deliver the second biocompatible material to the surface via a medical gas at a second medical gas pressure which is lower than the first pressure;

the regulation system further including a default position arranged to expel medical gas in the vicinity of the first and second biocompatible agent outlets in the absence of delivery of any biocompatible agent;

and wherein the regulation system includes at least one switch, operable by a user of the device, each switch biased such that in the absence of its activation by a user of the device the regulation system is set at the default position.

2. A device as in claim 1, constructed and arranged to deliver each of the first and second biocompatible agents to the surface via a single medical gas which also is expelled from the device in the default position.

3. A device as in claim 2, wherein the regulation system includes switching apparatus operable by a user of the device, interconnected such that when the device is activated in a preset treatment position, at least one other preset treatment position is inactivatable.

4. A device as in claim 3, wherein the switching apparatus is interconnected such that in the first preset treatment position the second preset treatment position is inactivatable and vice versa, and in the third preset treatment position the fourth preset treatment position is inactivatable and vice versa.

5. A device as in claim 1, comprising at least two ports connectable to at least two separate reservoirs of biocompatible agent, each port fluidly connected to a conduit including a biocompatible agent outlet adapted to emit biocompatible agent in an orientation allowing medical gas emitted from the outlet of a gas conduit to carry biocompatible agent to the surface.

6. A device as in claim 1, further comprising at least two separate reservoirs of biocompatible agent, and at least two ports connectable to the at least two separate reservoirs of biocompatible agent, each port fluidly connected to a separate biocompatible agent conduit including a separate outlet.

7. A device as in claim 6, wherein each of the at least two separate reservoirs is connectable to a source of pressurized medical gas.

8. A device as in claim 6, wherein each of the at least two separate reservoirs is connectable to the source of pressurized medical gas to which the gas conduit is connectable.

9. A device as in claim 8, further comprising a source of medical gas at a pressure greater than atmospheric pressure, connected to the gas conduit and connected to the at least two separate reservoirs.

10. A device as in claim 6, wherein the at least two separate reservoirs contain at least two agents that, when provided in combination, can form a medically-acceptable coating on a tissue surface of a patient.

11. A device as in claim 10, wherein at least one of the at least two agents comprises a synthetic polymer.

12. A device as in claim 10, wherein each of the at least two agents comprises a synthetic polymer.

13. A device as in claim 10, wherein each of the at least two agents consists essentially of a synthetic polymer.

14. A device as in claim 10, wherein the at least two agents comprise a first biocompatible agent that is a photoinitiator, and a second biocompatible agent.

15. A device as in claim 14, wherein the second biocompatible agent is polymerizable upon activation by the photoinitiator.

16. A device as in claim 10, comprising a first biocompatible agent inlet port and a second biocompatible agent inlet port connectable, respectively, to a first detachable biocompatible agent reservoir and a second detachable biocompatiblo agent reservoir.

17. A device as in claim 16, wherein each of the first and second biocompatible agent reservoir comprises a syringe housing.

* * * * *